US00PP14078P29

(12) United States Plant Patent
Drewlow

(10) Patent No.: US PP14,078 P2
(45) Date of Patent: Aug. 19, 2003

(54) KALANCHOE PLANT NAMED 'FOREVER MAXI SUNRAY YELLOW'

(75) Inventor: Lyndon W. Drewlow, Santa Barbara County, CA (US)

(73) Assignee: Oglevee, Ltd., Connellsville, PA (US)

( * ) Notice: Subject to any disclaimer, the term of this patent is extended or adjusted under 35 U.S.C. 154(b) by 55 days.

(21) Appl. No.: 09/877,298

(22) Filed: Jun. 8, 2001

(51) Int. Cl.[7] ..... A01H 5/00
(52) U.S. Cl. ..... Plt./338
(58) Field of Search ..... Plt./338, 335

*Primary Examiner*—Bruce R. Campell
*Assistant Examiner*—June Hwu
(74) *Attorney, Agent, or Firm*—Webb Ziesenhiem Logsdon Orkin & Hanson, P.C.

(57) ABSTRACT

A new Kalanchoe cultivar named 'Forever Maxi Sunray Yellow' characterized by the combined features of yellow colored flowers and excellent lateral and basal branching.

1 Drawing Sheet

Botanical classification: *Kalanchoe blossfeldiana.*
Varietal denomination: 'Forever Maxi Sunray Yellow'.

The present invention relates to a new and distinct cultivar of Kalanchoe plant, botanically known as *Kalanchoe blossfeldiana,* and known by the cultivar name 'Forever Maxi Sunray Yellow', Breeder No. 97-153-7. 'Forever Maxi Sunray Yellow' was discovered through controlled breeding by crossing Mikkelsen Seedling No. 93-146-10 (seed parent, unpatented) and Mikkelsen Seedling No. 93-118-1 (pollen parent, unpatented) in Ashtabula, Ohio.

Asexual reproduction of stem cuttings taken in Lompoc, Calif. has shown that the unique features of this new Kalanchoe are stabilized and are reproduced true to type in successive propagations.

The following characteristics distinguish the new Kalanchoe from both its parent varieties and other cultivated Kalanchoes of this type known and used in the floriculture industry, namely, 'Goldstrike' (U.S. Plant Pat. No. 6,632) and 'Revelry' (U.S. Plant Pat. No. 7,795).

1. 'Forever Maxi Sunray Yellow' has Yellow Group 7B colored flowers which are similar to 'Revelry' compared to 'Goldstrike' being a golden yellow, Yellow-Orange Group 15B.
2. 'Forever Maxi Sunray Yellow' is a taller growing cultivar at 18 cm than 'Goldstrike' at 14 cm and 'Revelry' at 12 cm.
3. 'Forever Maxi Sunray Yellow' has larger flowers (18 mm wide) than 'Goldstrike' and 'Revelry' (15 mm wide each).
4. 'Forever Maxi Sunray Yellow' has an obovate leaf shape being almost round while 'Goldstrike' and 'Revelry' have ovate leaves.
5. 'Forever Maxi Sunray Yellow' has shallower crenate lobing of the leaves than either 'Goldstrike' and 'Revelry' which have deeper crenate lobing.
6. 'Forever Maxi Sunray Yellow' has a shorter flowering response time of 8.5–9 weeks in the summer and 10–10.5 weeks in the winter than 'Goldstrike' and 'Revelry' which are both 1.5 weeks later to bloom in both seasons.
7. 'Forever Maxi Sunray Yellow' flowers keep up to 7 days longer under home conditions than 'Goldstrike' and 'Revelry'.

The accompanying colored photograph illustrates the overall appearance of this cultivar taken as a face view of the plant and showing the colors as true as it is reasonably possible to obtain in a colored reproduction of this type.

The following is a detailed description of the new cultivar, based on plants produced at Oglevee, Ltd. in greenhouses in Lompoc, Calif. during the Winter season of the year. Plants were grown in 10 cm pots and measurements and photographs were taken 13 weeks after rooted cuttings were planted. Height measurements were taken from the soil line of the container. The plants were grown at 16° C. night temperatures, 3000–4000 foot candles of light, and 200 ppm nitrogen, 75 ppm potassium, and 200 ppm phosphorous nutritional levels, with trace elements added. The plants were not treated with growth regulators. Habit of growth, foliage coloration, leaf variegation, size of leaves, and peduncle length will be greatly influenced by nutritional and environmental conditions.

Color references are made to The Royal Horticultural Society Colour Chart except where general terms of ordinary dictionary significance are used.

Parentage: A controlled cross between female parent Mikkelsen Seedling No. 93-146-10 by male parent Mikkelsen Seedling No. 93-118-1.

Propagation:

(*A*) *Type cutting.*—Stem tip cuttings up to 3 cm long.
(*B*) *Time to root.*—10 days at 21° C. summer; 12 days at 21° C. winter.
(*C*) *Rooting habit.*—Fine, fibrous, abundant.

Plant description:

*Habit and form of growth.*—Semi-tall, semi-mounded; excellent basal branching; flower clusters bloom above foliage. Environment and use of growth regulators will play a role in final height. Average plant height is 18 to 20 cm, average plant width is 28 to 30 cm.

*Foliage description.*—Leaves simple and opposite. Size: Average, full grown leaves on a plant when grown in a 10 cm pot are 7 to 8 cm long and 7 to 8 cm wide. Shape: Obovate with obtuse apex and rounded to truncate base. Texture: Glabrous; coriaceous and succulent. Margin: Crenate; shallow lobed. Color: Young foliage top side is Yellow-Green Group 146A, underside is Yellow-Green Group 146B; mature foliage top side is Yellow-Green Group 147A, underside is Yellow-Green Group 147B.

Flowering description:

*Flowering habits.*—Inflorescence is a compound dichasial cyme. Terminal flower on main axis opens first followed by the terminal flowers of the side branches, continuing with the subsequent development of branches in the inflorescence. Inflorescence is made up of the main stem and up to 8 or more lateral branches depending on growing schedule followed.

*Natural flowering season.*—Early January. Flowering time under controlled daylength at 20° C. in summer is 8.5 to 9 weeks; in winter is 10 to 10.5 weeks. Flowering time depends on temperature, light intensity, and other growing conditions

*Flower lastingness.*—10–14 days for an individual flower.

*Flower buds.*—Oblong, up to 1.1 cm long before showing color, developing to tubular as flower petals mature; sheathed in four sepals colored Yellow-Green Group 144B.

*Flowers borne.*—Compound dichasial cyme with primary peduncle being 4 mm in diameter just below the first branch of the inflorescence; length of peduncle will vary depending on growing conditions. Pedicels vary in length depending on where they are in the inflorescence. External secondary branch pedicels vary between 2 mm to 3 mm.

*Quantity of flowers.*—Numerous long-lasting flowers as main stem plus the 8 or more lateral branches will have 30 or more flowers each.

*Petals,*—Shape: Almost round, top cuspidate. Color: Top side when opening is Yellow Group 6A, fading to Yellow Group 7B; underside is Yellow Group 6D. Number of petals: 4. Size of individual petals: 8 mm wide and 9 mm long.

*Sepals.*—Shape: lanceolate. Surface texture: glabrous. Size: 5 mm long and 2 mm wide.

*Reproductive organs.*—Stamens: 8 in number. Anthers: Flat, elliptical in shape, yellow-green in color, 153C. Filament color: Yellow-green, 146D. Pollen: Yellow in color, 15A; abundant. Pistils: Stigma: Flat in shape, mature color is white, 155A. Style color: Green, 146D. Ovaries: 4 in number, immature size 7 mm, green color, 146B.

*Seed formation.*—Seed formation occurs only under controlled crossings with 100 or more very small seeds per ovary present. However, this is not a seed grown crop.

Disease resistance: 'Forever Maxi Sunray Yellow' has shown resistance to powdery mildew. No disease problems have been observed to date.

OTHER IMPORTANT CHARACTERISTICS

1. Semi-tall growth combined with good lateral and basal branching allows cultivar to be finished in a 15 cm pot from one cutting instead of the usual three cuttings.

2. Excellent flower coverage on upper half of plant due to excellent lateral and basal branching.

3. No growth regulators are needed to grow this cultivar.

I claim:

1. A new and distinct cultivar of Kalanchoe plant named 'Forever Maxi Sunray Yellow', as illustrated and described.

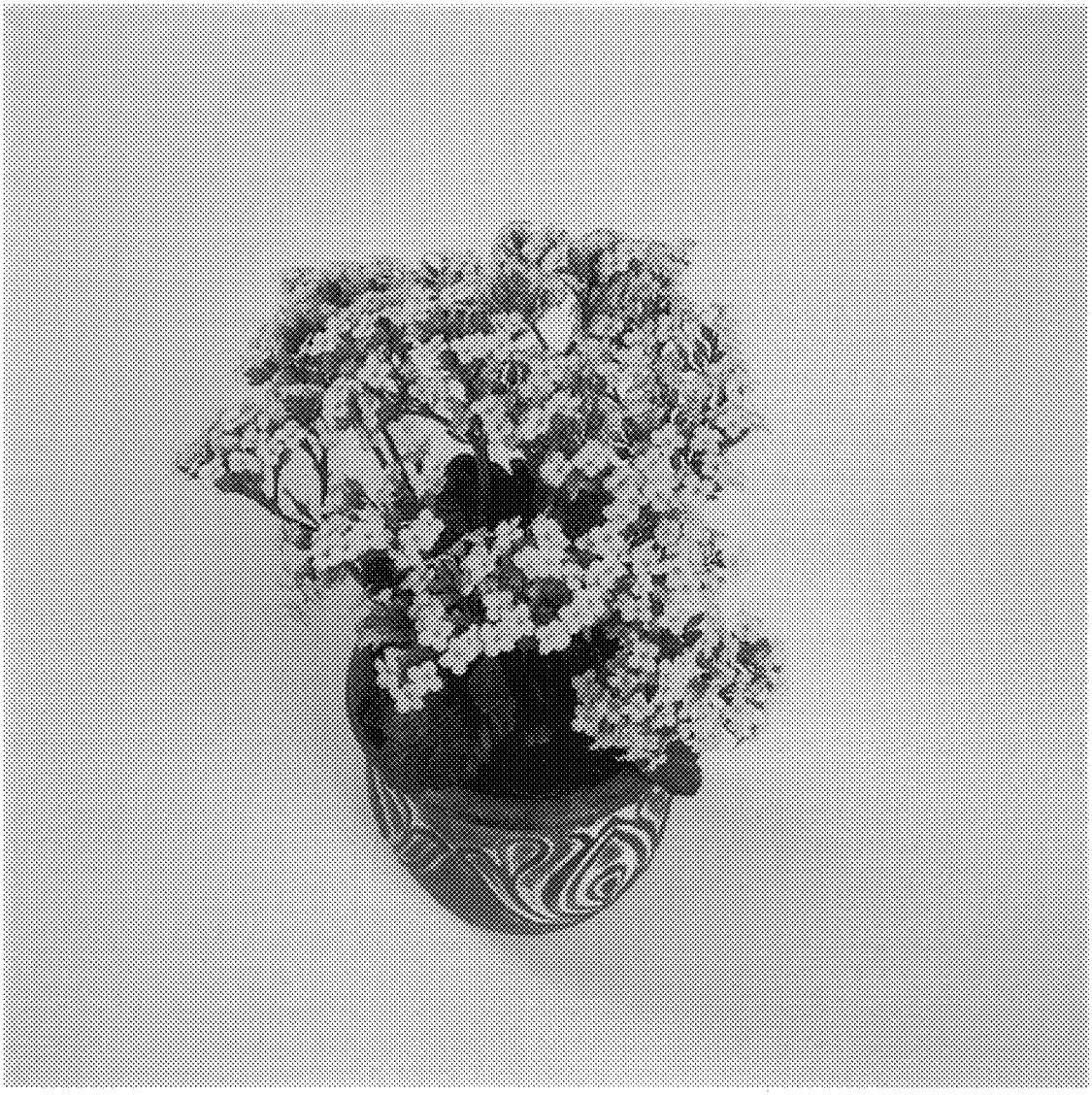

* * * * *